(12) United States Patent
Orlov

(10) Patent No.: US 11,925,807 B2
(45) Date of Patent: Mar. 12, 2024

(54) METHODS FOR OPERATING A DUAL-CHAMBER PACEMAKER TO AVOID TRIGGERING ATRIAL FIBRILLATION AND PERPETUATION OF REPETITIVE VENTRICULO-ATRIAL SYNCHRONY

(71) Applicant: Michael V Orlov, Brookline, MA (US)

(72) Inventor: Michael V Orlov, Brookline, MA (US)

( * ) Notice: Subject to any disclaimer, the term of this patent is extended or adjusted under 35 U.S.C. 154(b) by 302 days.

(21) Appl. No.: 17/477,396

(22) Filed: Sep. 16, 2021

(65) Prior Publication Data

US 2022/0080201 A1 Mar. 17, 2022

Related U.S. Application Data

(60) Provisional application No. 63/079,790, filed on Sep. 17, 2020.

(51) Int. Cl.
| | | |
|---|---|---|
| *A61N 1/362* | (2006.01) | |
| *A61N 1/365* | (2006.01) | |
| *A61N 1/368* | (2006.01) | |

(52) U.S. Cl.
CPC ....... *A61N 1/3682* (2013.01); *A61N 1/36585* (2013.01)

(58) Field of Classification Search
CPC . A61N 1/3682; A61N 1/36585; A61N 1/3624
See application file for complete search history.

(56) References Cited

U.S. PATENT DOCUMENTS 6,498,949 B2 * 12/2002 Levine ................ A61N 1/3622
607/9

FOREIGN PATENT DOCUMENTS

WO WO-2006065707 A2 * 6/2006 ......... A61B 5/04525

OTHER PUBLICATIONS

Sharma PS et al. Repetitive nonreentran tventriculoatrial synchrony: An underrecognized cause of pacemaker-related arrhythmia. Heart Rhythm 2016;0;1-9.
Alasti M et al. Pacemaker-mediated arrhythmias. J Arrhythmia 2018;1-8.

(Continued)

*Primary Examiner* — Brian T Gedeon
(74) *Attorney, Agent, or Firm* — Boris Leschinsky

(57) ABSTRACT

Pacemaker-initiated atrial fibrillation during competitive atrial pacing is a common arrhythmia with potentially serious consequences The novel pacing method proposes a novel way to automatically detect and diagnose competitive atrial pacing, and to deliver an intervention via a pacing stimulus in the atrium simultaneously with delivering a pacing stimulus in the ventricle, and doing this after a longer waiting period. By doing this, potentially hazardous scenarios causing atrial fibrillation in competitive atrial pacing are avoided, while the rhythm regularity and the synchrony between the upper and lower chambers of the heart are maintained. At the same time, the vicious cycle of retrograde conduction from the ventricle to the atrium—the culprit of the problem—is terminated and not allowed to reoccur for several subsequent cardiac cycles, thereby preventing the extended propagation of repetitive non-reentrant ventriculo-atrial synchrony.

12 Claims, 3 Drawing Sheets

(56) References Cited

OTHER PUBLICATIONS

Barold SS et al. Case report: complex arrhythmia induced by noncompetitive atrial pacing algorithm of DDDR pacemaker. J Interv Card Electrophysiol Dec. 2001;5(4):431-4. Abstract.
Orlov MV et al. Is competitive atrial pacing a possible trigger for atrial fibrillation? Observations from the RATE registry. Heart Rhythm 2020, 1-7.

* cited by examiner

METHODS FOR OPERATING A DUAL-CHAMBER PACEMAKER TO AVOID TRIGGERING ATRIAL FIBRILLATION AND PERPETUATION OF REPETITIVE VENTRICULO-ATRIAL SYNCHRONY

CROSS-REFERENCE DATA

This application claims a priority benefit of the U.S. Provisional Patent application No. 63/079,790 filed Sep. 17, 2020 by the same inventor and with the same title, which is incorporated herein by reference in its entirety.

FIELD OF THE INVENTION

This invention proposes a new algorithm for operating an implantable cardiac rhythm management device such as various pacemakers, defibrillators, ICDs and alike, cumulatively referred to as a pacemaker. These devices use numerous algorithms to adjust cardiac rhythm by utilizing pacing—delivering small electrical impulses to the heart. More specifically, the invention pertains to operating a dual-chamber pacemaker configured to pacing a cardiac atrium using the first "atrial" channel and a cardiac ventricle using a second "ventricular" channel. Occasionally, deleterious effects from these algorithms can be observed and can harm the patient. One of these potential harms is induction of a new arrhythmia facilitated by the pacing device itself, not by any underlying heart conditions of the patient. One example of this is Competitive Atrial Pacing (CAP) that can occur in all current implantable cardiac rhythm management devices and can potentially trigger atrial fibrillation (a dangerous cardiac arrhythmia) as described in the following two references: (a) Orlov M V, Olshansky B, Benditt D G, Kotler G, McIntyre T, Qu F, Turkel, M, Gorev M, Poghosyan H, Waldo A L. Is Competitive Atrial Pacing a Possible Trigger for Atrial Fibrillation? Observations from the RATE Registry, *Heart Rhythm* (2020), doi: https://doi.org/10.1016/j.hrthm.2020.07.028, and (b) Sharma P S, Kaszala K, Tan A Y, et al. Repetitive nonreentrant ventriculoatrial synchrony: An underrecognized cause of pacemaker-related arrhythmia. *Heart Rhythm* 2016; 13:1739-1747. doi.org/10.1016/j.hrthm.2016.04.002.

This invention proposes a new algorithm to avoid the induction of device-initiated (during CAP) atrial fibrillation—the most common arrhythmia with potentially serious consequences—and also immediately terminate the repetitive cycle of CAP, thereby providing the first algorithm for reliable CAP termination.

BACKGROUND

Modern implantable pacemakers use highly sophisticated algorithms in the attempt to mimic normal physiological functions of the human heart and to provide smooth transitions in case of heart rhythm irregularities. The main pacing function of these devices is to support the heart if the rhythm slows down. Sophisticated algorithms provide backup pacing when the heart is very slow but can also help if patients have lost the ability for adequate heart rate response to exercise.

This functionality will provide faster paced heart rates that are needed during any kind of physical activity. However, patient's own heart can frequently compete with paced rhythms delivered by a pacemaker—this is called competitive pacing. Competitive pacing is most frequently observed when pacemakers stimulate the upper chambers of the heart—atria—hence, the term Competitive Atrial Pacing (CAP). This situation cannot be avoided in modern implantable pacemakers for a number of reasons. Manufacturers have developed several algorithms to prevent this (Alasti, M, Machado, C, Rangasamy, K, et al. Pacemaker—mediated arrhythmias. J Arrhythmia. 2018; 34: 485-492. https://doi.org/10.1002/joa3.12098). These modifications are based on changing the timing of various pacing events in the upper and lower chambers of the heart. Unfortunately, these measures are frequently ineffective (see Orlov et al, Sharma et al cited above as well as Barold S S, Levine P A, Isaeff D M, Betzold R. Case report: complex arrhythmia induced by noncompetitive atrial pacing algorithm of DDDR pacemaker. *J Interv Card Electrophysiol* 2001; 5 (4):431-4. PMID: 11752911). Moreover, CAP was recently shown by us to be able to trigger dangerous cardiac arrhythmias such as atrial fibrillation (see Orlov et al as cited above). Therefore, development of an algorithm modification that would avoid potential triggering of atrial arrhythmias would be highly desirable.

The extent of the problem is significant. According to the RATE Registry data, as much as 23.4% of patients having a pacemaker device have experienced CAP. In addition, the registry demonstrated a close and statistically significant association of CAP and AF, with AF occurring in as many as 71% of patients with CAP. It is also shown that CAP triggers AF in 61.8% of all arrhythmia episodes. Avoidance of CAP and AF would be highly beneficial and, among other benefits, may allow for reduction of anticoagulation levels.

The problem is also not specific to any one pacemaker manufacturer. None of the current pacemakers have any methods for termination of repetitive non-reentrant ventriculo-atrial synchrony, which is needed to address the problem.

SUMMARY

Process of electrical excitation in the cardiac tissue is characterized by a phenomenon called "a vulnerable period". This occurs during every heartbeat. If an electrical impulse is delivered artificially by a pacemaker during this period it can potentially trigger an arrhythmic response (dangerous arrhythmia). During CAP, a potential exists to deliver a pacing stimulus within that "vulnerable period". Timing is particularly important in this situation and therefore delivering such a pacing stimulus outside of this "vulnerable period" may potentially avoid triggering of dangerous arrhythmias such as atrial fibrillation.

Existing algorithms try to avoid this potentially dangerous situation in two different ways:
1. By extending the waiting period from a previous pulse by approximately 300-400 msec before the next pacing stimulus in the atrium is delivered (which is followed by pacing the ventricle—the bottom chamber of the heart—after another delay of approximately 200 msec in order to maintain the synchrony between the top and the bottom chambers), or
2. By avoiding pacing the atrium altogether (in that case just the bottom chamber of the heart will be stimulated by the implantable device).

These techniques do not always work as intended. Extending the timing before the next pacing stimulus is delivered may still not avoid the "vulnerable period", as documented previously (See Orlov et al and Sharma et al as cited above). Avoiding pacing the atrium altogether may result in another device-triggered arrhythmia commonly known as "pacemaker-mediated tachycardia".

The novel pacing method of the present invention proposes to deliver the pacing stimulus in the atrium simultaneously with delivering a pacing stimulus in the ventricle and doing this after a longer waiting period. By doing this, both of the two potentially hazardous scenarios described above can be avoided, while maintaining the rhythm regularity and the synchrony between the upper and lower chambers of the heart. At the same time, the vicious cycle of retrograde conduction from the ventricle to the atrium—the culprit of the problem—is terminated and not allowed to reoccur for several subsequent cardiac cycles, thereby preventing the extended propagation of repetitive non-reentrant ventriculo-atrial synchrony (RNRVAS).

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF PREFERRED EMBODIMENTS

Figure 1:
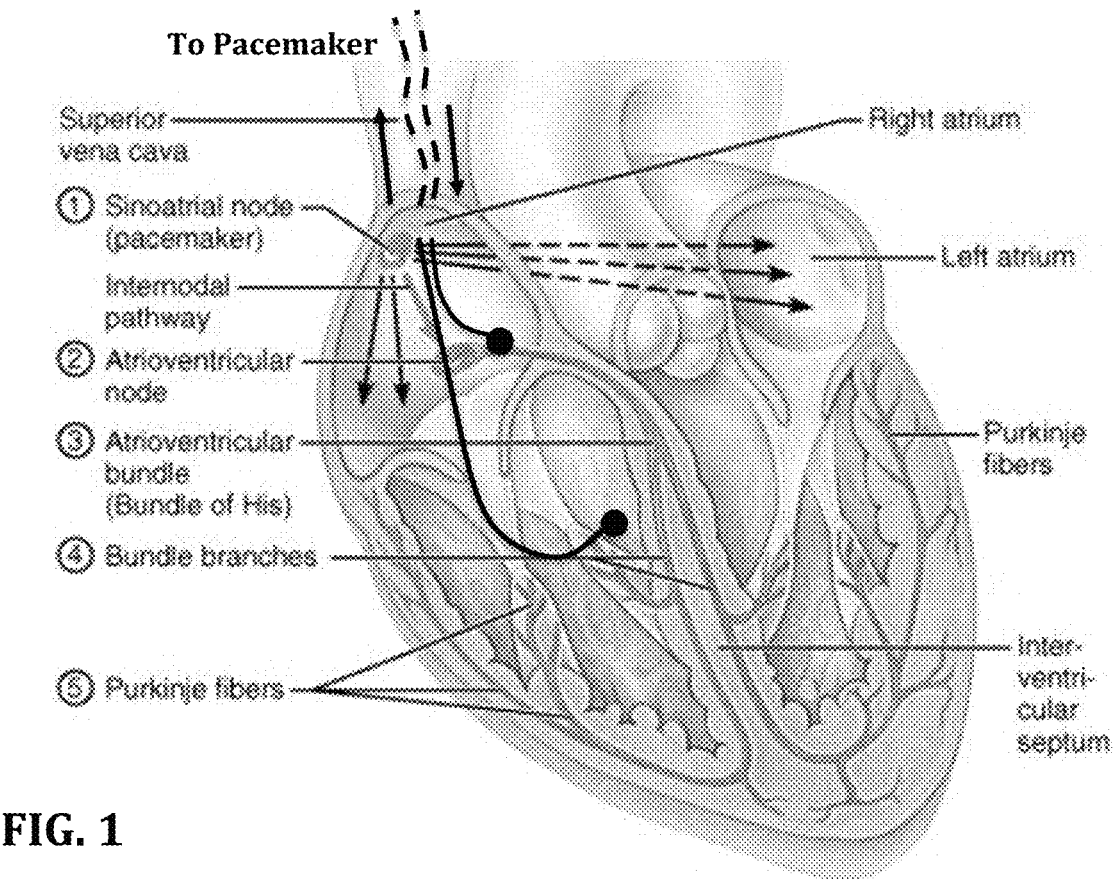
FIG. 1 shows a schematic anatomy of the heart, it's electrical conduction system and illustration of pacemaker wires location and basic function.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

FIG. 1 shows a schematic anatomy of the heart, it's electrical conduction system and illustration of pacemaker wires location and basic function. Two upper chambers of the heart—right and left atrium—RA and LA. Two bottom chambers of the heart—right and left ventricles—RV and LV. Native electrical impulse is formed in the specialized cells in the RA before every heartbeat and slowly conducted to both top chambers by specialized tracks consisting of conduction cells. Eventually, the impulse travels to the middle of the heart slowly conducting through the atrio-ventricular node and then via specialized conduction bundles down to the ventricles. Thus, in the normal heart there is a normal time delay between the excitation of the top and bottom chambers of the heart, typically not more than 200 msec. Pacemaker electrodes are schematically shown to be connected to the upper chamber—RA, and the bottom chamber—RV. Sensed intrinsic electrical events from the heart are conducted back to the pacemaker (arrows pointing towards the pacemaker from the heart) and pacing stimuli from the pacemaker are sent to the heart both to the atrium and the ventricle with the appropriate time delay to simulate the slow conduction from the top chambers to the bottom chambers in the native heart (arrows pointing from the pacemaker to the heart).

Figure 2:
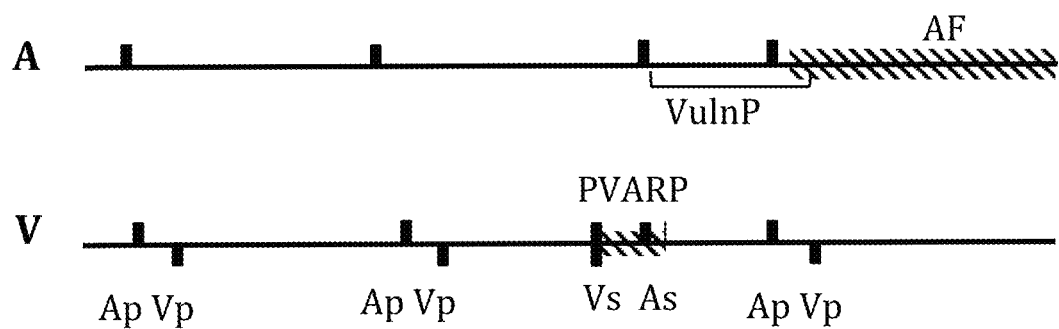
FIG. 2 shows a first common scenario during the competitive atrial pacing with atrial stimulus (Ap) being delivered at the predetermined interval after a "sensed event" in the atrium.

FIG. 2 illustrates a first common scenario during the competitive atrial pacing with atrial stimulus (Ap) being delivered at the predetermined (by the programmed pacing rate) interval after a "sensed event" in the atrium during post ventricular atrial refractory period (PVARP)—pacemaker is trying to compete with intrinsic heart rate in order to satisfy the perceived needs of the human body during exercise as atrial events sensed during PVARP are not used to time the next pacing stimulus. Ap event occurs after a delay determined by the programmed lower rate or the rate indicated by the pacemaker's sensor and is followed by a ventricular stimulus (Vp) in order to maintain the synchrony between the top and the bottom chambers. Potential "vulnerable period" (VulnP) is shown. Ap stimulus delivered during the VulnP can trigger arrhythmia if appropriately timed. Triggering of arrhythmia (atrial fibrillation—AF) by delivering Ap during the "vulnerable period" is shown here and also in FIG. 5. Existing algorithms (N-CAP, PVC response, Atrial Flutter Response) allow to extend this waiting period before Ap-Vp sequence by some programmable value (typically, 200-400 msec) but cannot always prevent repetition of CAP and potentially triggering of atrial fibrillation. There are no specific algorithms to recognize and terminate CAP or its specific and most common form, repetitive non-reentrant ventriculo-atrial synchrony (RNRVAS).

Figure 3:
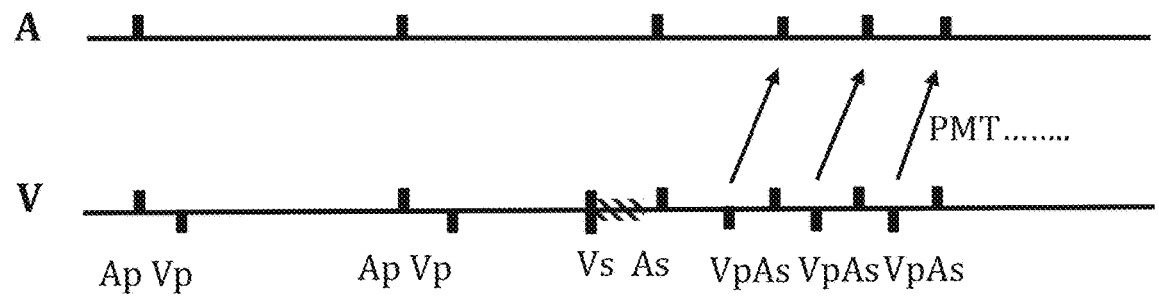
FIG. 3 shows a second common scenario, in which avoiding atrial pacing altogether triggers a "pacemaker-mediated tachycardia"

FIG. 3 shows a second common scenario: by avoiding atrial pacing altogether and only delivering the ventricular stimulus (Vp) after a sensed event in the atrium outside of PVARP another problem may be triggered—the so-called "pacemaker-mediated tachycardia" or endless loop tachycardia (each Vp—ventricular stimulus—excites the ventricle and conducts retrogradely back to the atria—arrow, it is then sensed by the pacemaker and triggers another Vp event which in turn conducts again back to the atria and so forth, and so on). Atrial events sensed outside of PVARP may be used to trigger the next pacing stimulus in the ventricle and this may be deleterious and result in "pacemaker-mediated tachycardia". There are several algorithms designed to recognize and terminate this kind of pacemaker triggered arrhythmia.

Figure 4:
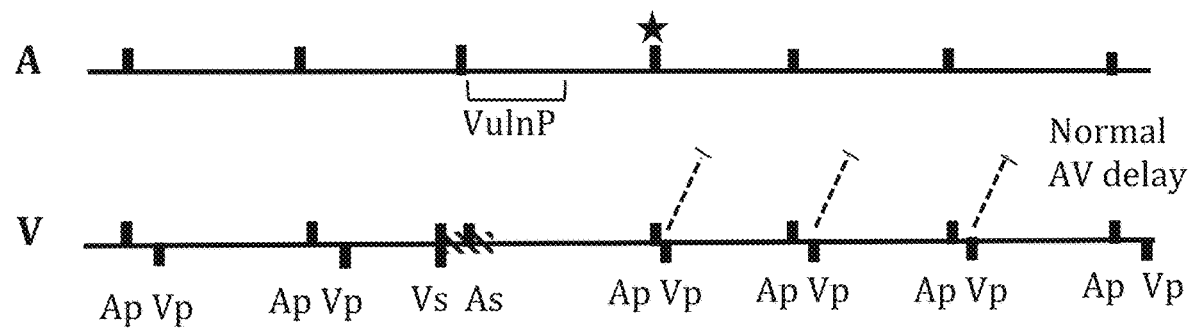
FIG. 4 illustrates pacing according to the proposed algorithm.

FIG. 4 shows schematically a proposed algorithm which avoids both of the above scenarios: Ap (atrial pacing stimulus shown by a star) is delivered simultaneously with Vp (ventricular pacing stimulus) after the "vulnerable period" by extending the waiting time further than 300-400 msec. This may occur over one or more cardiac cycles, in series or otherwise. This simultaneous pacing of Ap and Vp prevents an onset of atrial fibrillation by being outside of the "vulnerable period" and also avoids retrograde conduction back to the atria (shown by a dashed line and block in conduction) due to almost simultaneous excitation of both upper and lower chambers of the heart, which blocks retrograde conduction by two excitation wavefronts propagating towards each other and causing refractoriness both in antegrade and retrograde conduction pathways, that may last longer than 1 cardiac cycle. In subsequent beats, the delay between Ap and Vp is slowly extended in order to resume the normal timing relationships between pacing (and sensing) in both top and lower chambers of the heart while still maintaining the block in retrograde conduction by the mechanism mentioned above. Such slow increase in delay between Ap and Vp may occur over at least 1 subsequent cycle, at least 2 subsequent cycles, at least 3 subsequent cycles, at least 4 subsequent cycles, at least 5 subsequent cycles, at least 6 subsequent cycles, or over additional subsequent cycles, as the invention is not limited in this regard.

Figure 5:
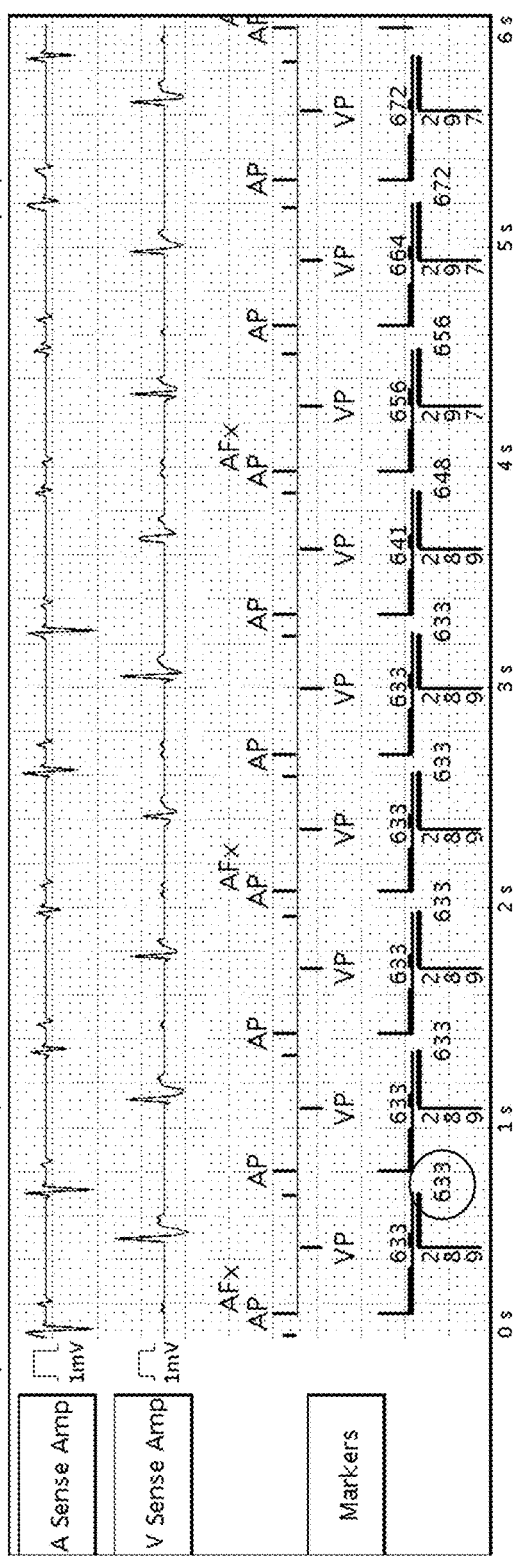
FIG. 5 shows a real-life example of the first common scenario as illustrated schematically in FIG. 2.
Figure 5:
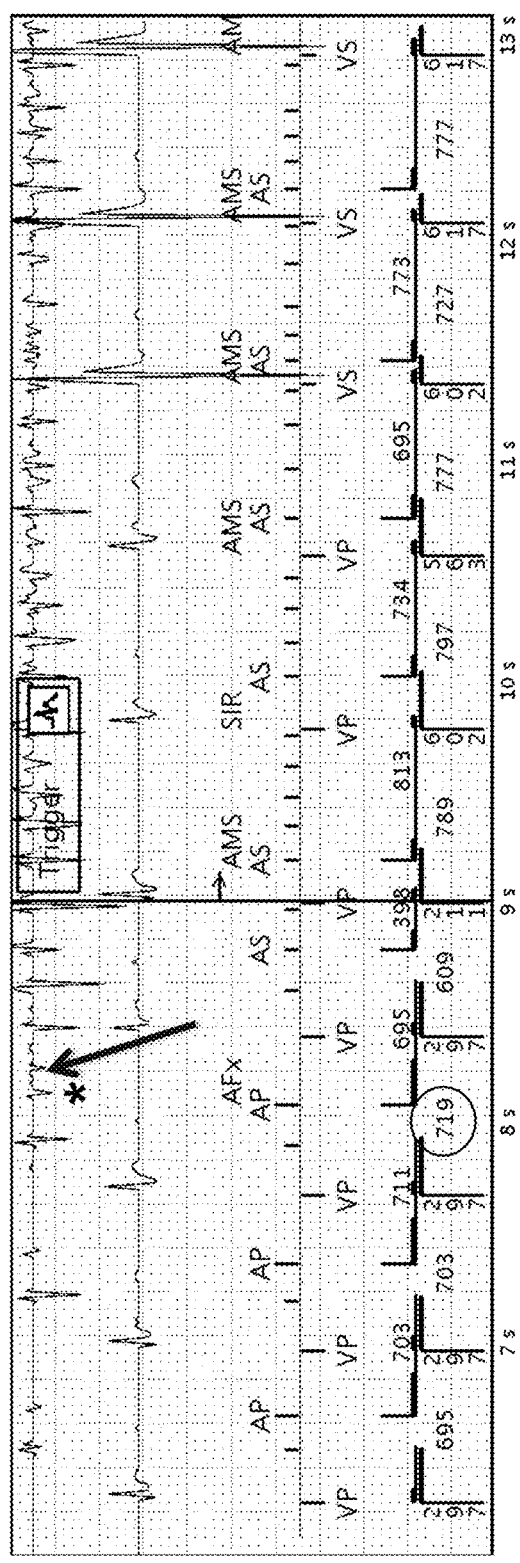

FIG. 5 shows a real-life example of the first common scenario. Ongoing CAP (RNRVAS) while an AFx algorithm (promotes faster atrial pacing rates) and sensor-indicated rate (SIR) (likely secondary to patient exercising) algorithms are active. Continuation of the same episode from the top to the bottom tracing demonstrates ongoing CAP. The $3^{rd}$ AP event with capture (asterisk, bottom tracing) is followed by an immediate initiation of atrial fibrillation (arrow). Note the gradual coupling interval prolongation between retrograde AS and AP events (numbers at the bottom—from 633 msec to 719 msec—circle) finally allowing an AP stimulus to fall into a vulnerable period and trigger AT/AF.

Abbreviations in FIG. 5:
AFx—AF suppression algorithm that promotes atrial pacing
AMS—Auto Mode Switch
AS—Atrial Sense, indicated by closely spaced short vertical lines after AMS
AR—Atrial Sense in refractory—indicated by short vertical lines after each VP event in this case
AP—Atrial Pace
SIR—Sensor Indicated Rate—pacing rate according to the rate adaptation algorithm (sensor)
VP—Ventricular Pace
VS—Ventricular Sense The recording of FIG. 5 further illustrates a possibility for an alternative method for detecting a set of conditions leading to AF, namely an alternative to scanning the PVARP and the vulnerable period. This alternative method comes from the observation mentioned above that the period between successive atrial stimulations is gradually increasing, in this case from 633 msec to 711 msec. Since these delays are generated within the pacemaker itself, one can put a surveillance loop on this value, such that in case the device detects a consistent increase in this interval from one beat to the next, the intervention as described above may be triggered without scanning the PVARP and the vulnerable period. One threshold for triggering activation of the algorithm of the present invention may be a detection of an unusually short As-Ap interval or a gradual increase in the duration of time between As and AP events over at least the successive 3 cardiac cycles, at least 4 successive cardiac cycles, at least 5 successive cardiac cycles, at least 6 successive cardiac cycles, at least 7 successive cardiac cycles, or over more than 7 cardiac cycles.

A further condition that may be used to trigger the intervention of the present algorithm is an unusually short duration of time between retrograde atrial sense (AS) and atrial pace (AP) events. This may indicate the onset of CAP. One useful measure of this phenomenon is retrograde As to Ap duration being at or less than about 30 percent of the present cardiac cycle duration. Expressing this interval as a percent of the cardiac cycle has an advantage of being reasonably independent of the heart rate of the patient. In further embodiments, the onset of CAP may be detected when retrograde As to Ap duration is at or less than about 25 percent, 20 percent, or 15 percent of the cardiac cycle duration.

Implantable cardiac rhythm management devices are used in various disease states to support failing electrical conduction system of the heart. They typically consist of several conducting wires (typically 2 or 3) and the impulse generator with multiple pacing and sensing functions. These devices are capable of delivering electrical impulses to the upper and lower chambers of the heart with the appropriate timing delay to simulate the natural slowing of the electrical conduction in the A-V node (FIG. 1). They are also capable of sensing the intrinsic electrical activity of the normal heart in order not to deliver electrical stimuli when not needed. These sophisticated functions require a number of timing periods during which the device is either waiting for the intrinsic electrical signals to occur (and does not deliver the pacing stimuli)—the so-called alert periods or does not deliver the pacing stimuli after the previous paced event no matter what—the so-called refractory periods.

The post-ventricular atrial refractory period (PVARP) is one of several refractory periods used in dual chamber pacemakers, it is initiated by ventricular sensing (Vs) or ventricular pacing (Vp) events and represents a programmable interval during which the atrial channel of a pacemaker is "blinded". Atrial events that may fall into the PVARP are not used to determine the timing of the next atrial pacing stimulus.

For this invention, PVARP is viewed as important for the normal pacemaker function but can also allow for a malfunction and occurrence of arrhythmias potentially triggered by the implantable cardiac rhythm management device itself. The PVARP refractory period occurs after a ventricular paced event (Vp—FIG. 2-4) and is used in particular to avoid sensing of retrogradely conducted electrical stimuli. If such stimuli are sensed, it might trigger an endless loop tachycardia or PMT (see FIG. 3).

Retrograde conduction from the ventricles to the atria can result in pacemaker mediated fast rhythms (pacemaker mediated tachycardia or PMT—FIG. 3)—when the pacemaker will sense this abnormal electrical event, interpret it as normal and generate a ventricular pacing (Vp) stimulus (after a programmed AV delay). This Vp in turn may conduct again retrogradely to the atria, be sensed again and generate the next Vp event, thus creating a basis for the so-called endless loop tachycardia or pacemaker mediated tachycardia. PVARP duration can be programmed differently and extending it typically allows to blind the pacemaker to the retrograde conduction, not trigger a Vp event following retrograde As event and thus to prevent PMT. Therefore, making PVARP longer (which blinds the pacemaker to retrogradely conducted events in the atrium) seems to be a solution for a number of problems that could be caused by an implantable cardiac rhythm management device. However, extending PVARP may create another set of problems: stimuli that are conducted retrogradely—back to the atria—will not be used to direct the pacemaker to pace the bottom chambers but still have to be counted in order to have an estimate of electrical activity in the atria (top chambers). In most devices atrial electrical events coinciding with the PVARP are not used to adjust the timing of the subsequent pacing stimuli to the top chamber. Therefore, atrial pacing (Ap—FIG. 2-5) can occur shortly after an atrial sensed event within the PVARP if dictated by the perceived need for faster heart rates—this occurs with competitive atrial pacing when an atrial event in the PVARP is sensed but ignored for timing purposes. Such a paced event in the atrium may: 1) encounter the atrial tissue still insensitive to electrical excitation from a previous electrical event (electrical cells require some time to recover their properties after previous excitation) or 2) occur during partial electrical recovery (vulnerable period) when it could potentially trigger an abnormal response or an arrhythmia, such as atrial fibrillation.

Pacing in Vulnerable Period—Consequences.

The electrical properties of heart cells and consequences of electrical stimuli delivered to them are now discussed in greater detail. If the cells have recovered from the previous excitation-conduction cycle, they will respond to an electrical impulse (either intrinsic or paced) with normal response—the next excitation-conduction cycle. However, if the next electrical impulse occurs prematurely, the cells will not have recovered their electrical properties and will be either completely inexitable (or refractory)—if it is very early after the prior excitation—or will be partially excitable by a stronger and somewhat later impulse—if they have partially recovered. This period when the cells are partially excitable is also called the vulnerable period, as the response to a premature electrical impulse may be abnormal and dangerous (FIG. 2, 5). Arrhythmias can be triggered by a pacing stimulus delivered during the vulnerable period. Therefore, an atrial pacing stimulus dictated by a pacing algorithm responsible for competitive atrial pacing can be deleterious (FIGS. 2 and 5 illustrate the occurrence of an arrhythmia—atrial fibrillation—after an atrial pacing stimulus delivered during the vulnerable period). We have recently shown a high incidence of this deleterious effect in a general pacemaker/ICD population (1).

Common Scenarios with Existing Algorithms in More Detail

There are existing pacing algorithms, developed to prevent or terminate such an abnormal pacemaker behavior. However, they are not sufficient. Some manufacturers have extended the alert period after a premature ventricular event to avoid pacing soon after a potential retrogradely conducted atrial event (this concept is illustrated in FIG. 2 where the alert period is extended by 200-400 msec). This algorithm can avoid pacing during the vulnerable period but sometimes the wait period may not be long enough, hence RNRVAS may be still triggered and further extension may conflict with other timing intervals. This algorithm works better after premature intrinsic ventricular beats (spontaneous) and will not avoid the occurrence of competitive atrial pacing. We and others have already shown that competitive atrial pacing is not avoided by these algorithms and can cause arrhythmias.

This invention proposes a different timing and sequence of stimulation after a sensed retrograde atrial event in the PVARP. Firstly, the waiting period is extended further than conventional 200-400 msec used in existing algorithms in order to avoid the vulnerable period. Secondly, atrial and ventricular pacing stimuli are delivered simultaneously following this extension (FIG. 4), typically within 0-20 milliseconds from each other. One advantageous consequence of such action is avoidance of retrograde conduction of the ventricular stimulus back to the atrium (this may trigger CAP) and likely blocking of such retrograde conduction for longer than 1 cycle thus breaking the vicious cycle of RNRVAS (repetitive form of CAP, see above).

In addition, the pacemaker may be configured to temporarily increase the output of atrial stimulation for the few cardiac cycles until the normal pacing conditions are restored. Such increase may be helpful to assure the most reliable capture of the atrium. In embodiments, the level of temporary increase in the stimulation level of the atrium during activation of the algorithm of the present invention may be at least 10% higher, at least 20% higher, at least 30% higher, at least 40% higher, at least 50% higher, at least 60% higher, at least 70% higher, at least 80% higher, at least 90% higher, at least 100% higher, or more as compared to the previous output of atrium stimulation. Once the normal pacing rhythm is restored, the output of electrical stimulation may be gradually or instantly returned to the pre-CAP values.

Subsequent stimulation sequence may include slow gradual separation between the atrial and ventricular pacing stimuli, thus bringing the atrial stimulus slightly forward (for example, advancing it by a set programmable number of milliseconds each cycle or beat) or gradually extending the AV interval (and introducing the Vp stimulus later) finally achieving traditional A/V synchrony as shown in FIG. 4. This allows to avoid retrograde conduction (if it is present) by creating a functional block in antegrade and retrograde conduction pathways, that will appear due to both excitation wavefronts (from the atrium going down to the ventricle, and from the ventricle going up to the atrium) meeting in the middle and creating a functional line of block (dashed line in FIG. 4 indicates functional block in retrograde conduction to the atrium). This functional block will persist for several cycles and terminate the repetitive cycle of RNRVAS for which there are no existing algorithms to terminate it (unlike PMT, which is readily recognized and terminated by existing device algorithms).

It is contemplated that any embodiment discussed in this specification can be implemented with respect to any method of the invention, and vice versa. It will be also understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. Incorporation by reference is limited such that no subject matter is incorporated that is contrary to the explicit disclosure herein, no claims included in the documents are incorporated by reference herein, and any definitions provided in the documents are not incorporated by reference herein unless expressly included herein.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12, 15, 20 or 25%.

All of the devices and/or methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

I claim:

1. A method for operating a dual chamber pacemaker configured for atrial and ventricular pacing, the method comprising the following steps:
   a. monitoring for:
      i. an onset of retrogradely conducted atrial electrical excitation recorded in post-ventricular atrial refractory period (PVARP), or
      ii. an increase in duration of time between retrograde atrial sense (AS) and atrial pace (AP) events over at least four successive cardiac cycles; or
      iii. a duration of time between retrograde atrial sense (AS) and atrial pace (AP) events is at or less than 30 percent of the present cardiac cycle duration;
   b. upon detection of either one of said events in step (a), extending an onset of atrial pacing stimulus by a predetermined interval, whereby avoiding atrial pacing during an atrial vulnerable period,
   c. regardless of the VA interval, initiating for the same cardiac cycle as in step (b) an onset of ventricular pacing stimulus to coincide with the onset of atrial pacing stimulus, whereby eliminating atrio-ventricular delay and blocking both atrio-ventricular and ventriculo-atrial electrical conduction allowing prevention of further occurrence of repetitive non-reentrant ventriculo-atrial synchrony (RNRVAS), and
   d. increasing the atrio-ventricular delay during at least 3 of the subsequent cardiac cycles after steps (b) and (c) from zero until reaching a physiologically acceptable value, while allowing for a change in heart rate,
   whereby interrupting onset or continuation of said retrogradely conducted atrial electrical excitation recorded in the PVARP as a cause of competitive atrial pacing and preventing an onset of atrial tachycardia or atrial fibrillation as a consequence thereof.

2. The method as in claim 1, wherein steps (b) and (c) are repeated for a subsequent cardiac cycle prior to proceeding to step (d).

3. The method as in claim 1, wherein steps (b) and (c) are repeated for two subsequent cardiac cycles prior to proceeding to step (d).

4. The method as in claim 1, wherein step (d) is extended over at least 4 of the cardiac cycles subsequent to completion of step (c).

5. The method as in claim 1, wherein step (d) is extended over at least 5 of the cardiac cycles subsequent to completion of step (c).

6. The method as in claim 1, wherein step (d) is extended over at least 6 of the cardiac cycles subsequent to completion of step (c).

7. The method as in step (b) further comprising a step of temporary increasing the output of atrial stimulation above the output of the previous cardiac cycle.

8. The method as in claim 7, wherein this temporary increase is removed once the normal rhythm is restored.

9. The method as in claim 7, wherein the temporary increase in atrial stimulation output is at least 50% higher than in the prior cardiac cycle.

10. The method as in claim 1, wherein in step (a) the duration of time between retrograde atrial sense (AS) and atrial pace (AP) events is at or less than 25 percent of the present cardiac cycle duration.

11. The method as in claim 1, wherein in step (a) the duration of time between retrograde atrial sense (AS) and atrial pace (AP) events is at or less than 20 percent of the present cardiac cycle duration.

12. The method as in claim 1, wherein in step (a) the duration of time between retrograde atrial sense (AS) and atrial pace (AP) events is at or less than 15 percent of the present cardiac cycle duration.

* * * * *